United States Patent
Dam

(10) Patent No.: US 8,714,017 B2
(45) Date of Patent: May 6, 2014

(54) APPARATUS FOR NON-INVASIVE DETERMINATION OF SOUND VELOCITY IN A LIQUID AND DETERMINING A PARAMETER OF THE LIQUID FROM THE SOUND VELOCITY

(75) Inventor: Naim Dam, Muttontown, NY (US)

(73) Assignee: HEMA-Q, Inc., Muttontown, NY (US)

( * ) Notice: Subject to any disclaimer, the term of this patent is extended or adjusted under 35 U.S.C. 154(b) by 345 days.

(21) Appl. No.: 13/296,314

(22) Filed: Nov. 15, 2011

(65) Prior Publication Data
US 2013/0304404 A1    Nov. 14, 2013

(51) Int. Cl.
*G01N 29/024*    (2006.01)

(52) U.S. Cl.
USPC .......................................... 73/597; 73/861.18

(58) Field of Classification Search
USPC ................... 73/597, 861.18, 861.27–861.31; 600/347, 438
See application file for complete search history.

(56) References Cited

U.S. PATENT DOCUMENTS

| | | | |
|---|---|---|---|
| 5,119,819 A | 6/1992 | Thomas | |
| 5,179,862 A | 1/1993 | Lynnworth | |
| 5,453,576 A | 9/1995 | Krivitski | |
| 5,685,989 A | 11/1997 | Krivitski | |
| 5,830,365 A | 11/1998 | Schneditz | |
| 6,029,507 A | 2/2000 | Faber | |
| 6,097,975 A * | 8/2000 | Petrovsky et al. | 600/316 |
| 6,165,151 A | 12/2000 | Weiner | |
| 6,550,345 B1 | 4/2003 | Letton | |
| 6,954,662 B2 * | 10/2005 | Freger et al. | 600/316 |
| 7,066,884 B2 * | 6/2006 | Custer et al. | 600/309 |
| 7,194,919 B2 * | 3/2007 | Shkarlet et al. | 73/861.18 |
| 7,481,114 B2 | 1/2009 | Lynnworth | |
| 7,608,043 B1 | 10/2009 | Lee et al. | |
| 7,838,296 B2 | 11/2010 | Corey | |
| 7,857,761 B2 * | 12/2010 | Lec et al. | 600/368 |
| 7,997,149 B1 | 8/2011 | Dam | |
| 8,235,897 B2 * | 8/2012 | Gal et al. | 600/365 |
| 2004/0054283 A1 | 3/2004 | Corey et al. | |
| 2006/0052963 A1 | 3/2006 | Shkarlef | |
| 2007/0255141 A1 | 11/2007 | Esenaliev | |
| 2011/0257530 A1 | 10/2011 | Tokita et al. | |
| 2011/0263956 A1 | 10/2011 | Gal et al. | |

OTHER PUBLICATIONS

J. Lubber and R. Graaff "A Simple and Accurate Formula for the Sound Velocity in Water" Ultrasonics in Medical & Biology, vol. 24, No. 7 p. 1065 (1998).

(Continued)

*Primary Examiner* — J M Saint Surin
(74) *Attorney, Agent, or Firm* — Leason Ellis LLP.

(57) ABSTRACT

Apparatus for determining the sound velocity of a liquid in a specimen having two walls between which the liquid is contained with one of the walls being deformable has a sensor including a transducer for transmitting ultrasonic energy signals between the specimen walls and apparatus for deforming the specimen wall by a known distance from a first to a second position relatively spaced from the transducer and an electronic circuit including a microprocessor for measuring first and second transit times of the signals through the liquid between the specimen walls for each of the specimen deformable wall first and second positions, and for calculating the sound velocity of the liquid based upon the known distance and the two measured transit times. Where blood is the liquid values of parameters such as glucose and hematocrit are obtained based on algorithms pre-programmed in the microprocessor.

24 Claims, 7 Drawing Sheets

(56) References Cited

OTHER PUBLICATIONS

"Determination of Velocity Ultrasonics in Whole Human Blood", 25th Annu. Conf. Eng, Med. Biol., Alliance for Engineering in Medicine and Biology, Bethesda, MD, Oct. 1972, p.

Bradley, D. L. and Sacerio, J. L. "The Velocity of Ultrasound in Human Blood under Varying the Physiologic Parameters", J. Surg. Res., 12, 290, 1972).

International Search Report mailed Mar. 15, 2013 for the corresponding PCT Application No. PCT/US2012/060418.

* cited by examiner

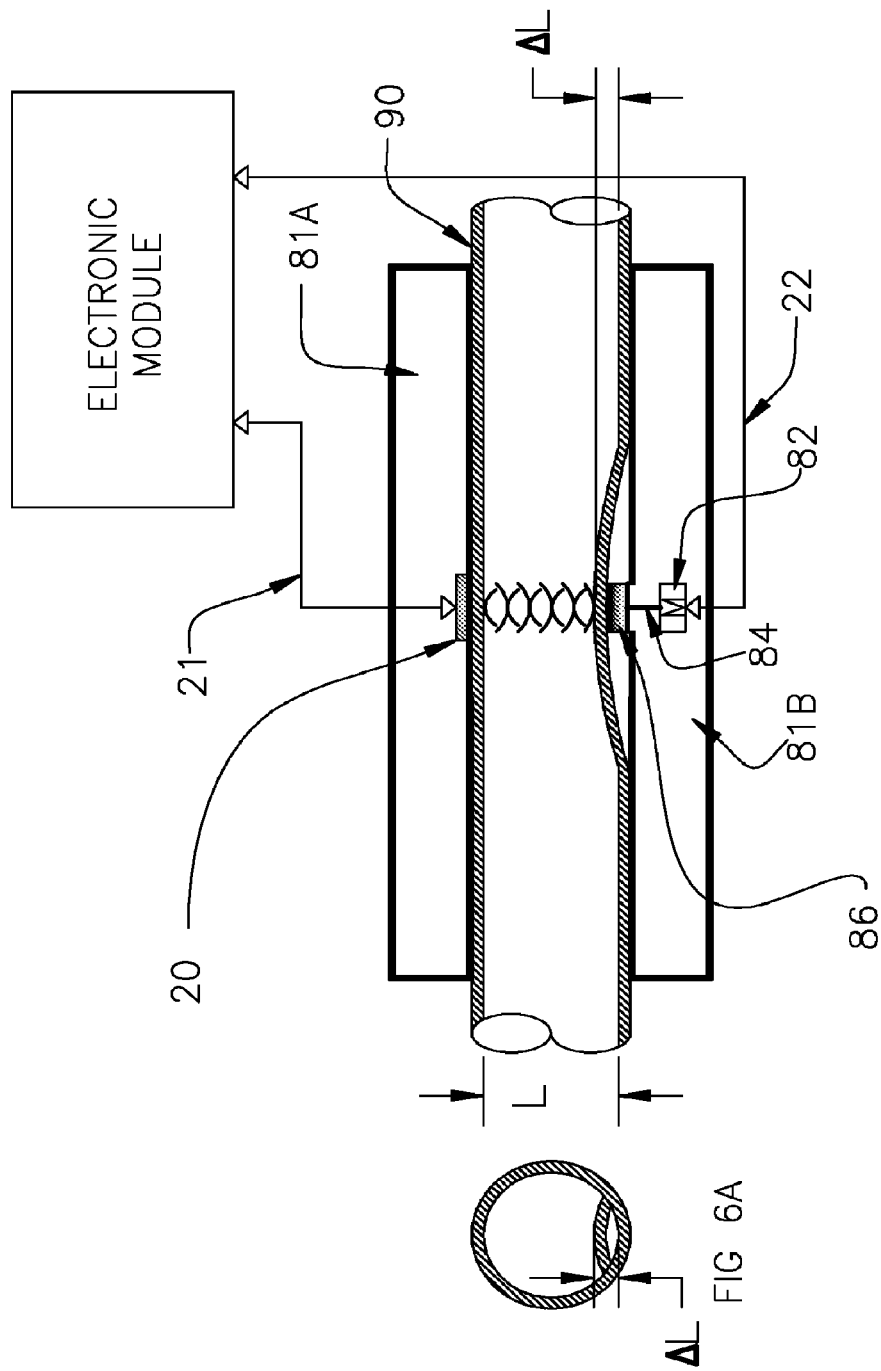
FIGURE: 6

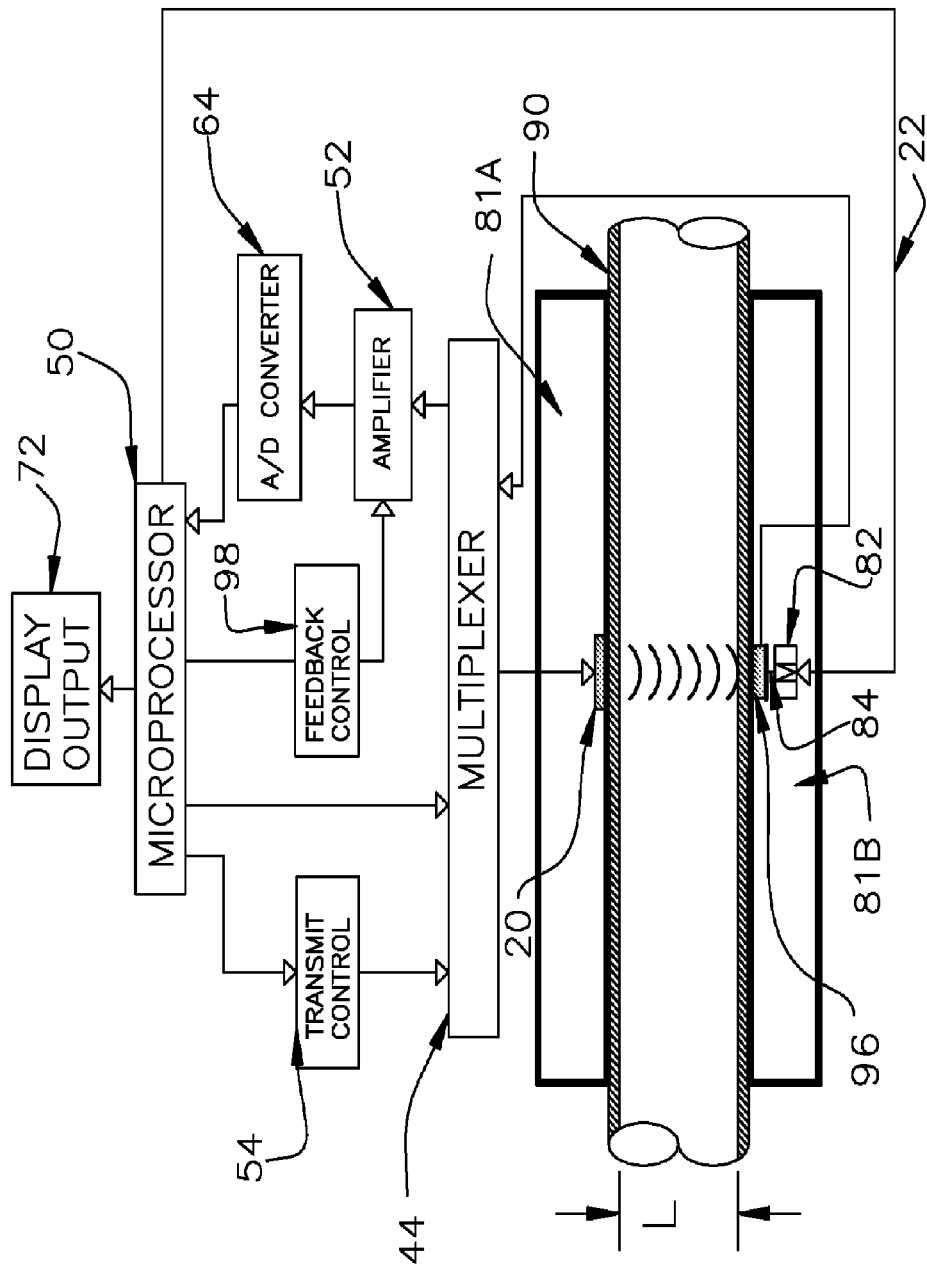
FIGURE: 7

APPARATUS FOR NON-INVASIVE DETERMINATION OF SOUND VELOCITY IN A LIQUID AND DETERMINING A PARAMETER OF THE LIQUID FROM THE SOUND VELOCITY

FIELD OF THE INVENTION

The present invention relates to an apparatus for non-invasively determining the sound velocity of a liquid contained in a specimen such as tissue or tubing having a deformable wall using an ultrasonic technique from which various parameters of the liquid, such as blood, in the specimen can be determined.

BACKGROUND OF THE INVENTION

Measuring the velocity of a signal in a liquid permits determination of many different characteristics or its properties. The velocity of the signal traveling in the liquid often is referred to as the "sound velocity", although frequencies of the signal energy measured can be different from typical sound frequencies in the audio range. The term "sound velocity" is used hereinafter to include all signal frequencies. Using the sound velocity together with appropriate mathematical relationships allows for determination of various characteristics or properties of the liquid such as its density, purity, concentration, components, etc.

Several different types of apparatus exist for measuring the sound velocity of a liquid present in a specimen. The term "specimen" is used hereinafter to define any receptacle or conduit having opposing walls, at least one of which is deformable, between which the liquid whose sound velocity is being measured is contained. The liquid in this specimen can be in a more or less static state or flowing through it. Examples of such specimens would be tissue of a human, such as an earlobe, in which blood is located in a substantially static state. Another is deformable plastic tubing in which a liquid is either static or flowing. Such tubing is used for a multitude of medical and industrial applications. The different types of apparatus for measuring sound velocity generally are classified as being of the contact or non-invasive type. In the contact type, some part or parts of the measuring apparatus come into direct contact with the liquid. In the non-invasive type, the sound velocity is measured without any part of the measuring apparatus coming into contact with the liquid.

In many applications it is preferred that the sound velocity measurement be made non-invasively so that the specimen does not have to be invaded and contact by an external member will not compromise the sterility or characteristics of the liquid. For example, in medical and biotechnology applications the non-invasive technique permits the sound velocity to be measured and from it various parameters of the liquid calculated using algorithms solved by a computer. The non-invasive technique permits this to be accomplished without having to invade the specimen to withdraw the liquid for analysis. Where blood is the liquid, typical parameters to be calculated are glucose and hematocrit values. The non-invasive technique also is useful to measure the sound velocity of hazardous chemicals and ultra pure liquids, such as are used in semiconductor processing systems. In such applications if an invasive technique is used where a part of the measuring apparatus comes in contact with the fluid, this might lead to contamination of the liquid and compromise its use in further processes. Also, when dealing with hazardous and corrosive fluids possible damage to parts of the measuring apparatus is avoided since there is no contact with the liquid.

Several instruments are known for making the sound velocity measurement non-invasively. For example, in U.S. pre-grant patent publication 2006/0052963 two pairs of ultrasonic transducers, or sensors, are used on opposing walls of the specimen. One of the sensors of each pair is a transmitter of ultrasonic (electro-mechanical) signal energy and the other is a receiver. The transmitting and receiving sensors of each pair are mounted on opposite sides of the specimen (tubing is shown) in which the fluid is flowing. The transit time of a signal from the transmitting sensor to the receiving sensor of each pair along a respective path through the fluid and the two specimen walls is measured. The sound velocity of the signal in the liquid is calculated from the results of the two transit time measurements. While such apparatus is effective in determining the sound velocity, it requires four sensors. Also, in some of the disclosed embodiments a special mounting is required for the sensors of the two pairs so that the transmitter and receiver sensors are offset at an angle from the tubing wall and from each other along the tubing length. Here the ultrasonic signal is transmitted by one sensor of each pair upstream and downstream of the fluid flow to the other sensor of the pair on the tubing opposite side.

In U.S. Pat. No. 7,481,114 a specimen in the form of flexible tubing is mounted in a fixture having a device that produces a force to deform the tubing external and internal dimensions at one point in a direction transverse to the tubing length. The tubing, or specimen, cross-sectional dimensions are hereafter referred to as "transverse length" since they are in a direction that is perpendicular to the tubing longitudinal axis and the fluid flowing in it. With the tubing not being deformed, there is a first acoustic path length in which a signal is transmitted by a transducer through both walls of the tubing and the transmitted signal is reflected back to the transducer. The force producing device is then operated to deform the normally circular flexible tubing cross section by a first amount to form a second acoustic path length. In the second acoustic path length a signal transmitted by the transducer is reflected from an inner wall of the deformed tubing back to the transducer. The round-trip transit times of the signal in both the first and second acoustic paths is measured and from this the patent disclosure indicates that the sound velocity can be computed although no specific teaching for doing this is given.

Non-invasive measurement has particular application when measuring the sound velocity of blood. For example, it is often necessary that one or more parameters of the blood of a person or animal be measured or monitored on a basis that requires a rapid determination of the parameter. For example, according to the International Diabetes Federation, more than 280 million people worldwide are currently living with diabetes and that number is expected to rise up to 438 million by 2030. People who have this disease must measure and monitor the level of glucose in the blood serum in order to control their disease, such as by change in diet or injection of a medication such as insulin. Presently, blood glucose most often is measured by taking a blood sample from a finger prick and applying the sample to an enzymatically medicated colorimetric test strip. The patient determines the glucose level based upon the color of the test strip. Many patients need to perform this procedure, which is annoying if not painful, several times per day. Also, the color measurement provides only a rough determination of the glucose level.

As another example, the measurement of the hematocrit blood parameter often is required. To accomplish this in the emergency/routine hospital environment, one or more blood samples are drawn from the patient, placed in vials and sent to a blood laboratory for analysis. Drawing of the blood causes the patient pain and discomfort. Also, since the blood has to be sent to a laboratory it means that the results are not available immediately. It often may require one hour or more waiting time. Patients requiring a rapid value measurement of a blood parameter, such as the hematocrit/hemoglobin value, sometimes are victims of a disaster events such as an auto accident. Such patients are undergoing trauma or are bleeding heavily in an emergency room. Accordingly, it would be desirable for medical personnel to react as promptly as possible when they need measurement of the hematocrit value to better react to the condition of the patient and sometimes even to save the patient's life. Therefore, it would be desirable to be able to determine the hematocrit value on a prompt basis that does not require drawing blood from the patient and sending it to a laboratory.

In yet another example where non-invasive measurement of sound velocity is advantageous, private practice physicians often need to screen a patient for possible anemia or other diseases. In such situations, a prompt determination of the hematocrit value is desirable so that a patient can be treated promptly, without having to draw a sample of the blood, wait for the laboratory results, and often have the patient make a return trip to the physician's office to learn the results and undergoing necessary treatment.

As should be apparent, a non-invasive technique for measuring sound velocity does not require extraction of blood from a patient. This advantageously does not subject the patient to the pain or discomfort caused by drawing blood to be placed in vials or by the pinprick extraction method. Also, by using the sound velocity measured by the non-invasive technique and appropriate computer based algorithms various blood parameters can be determined on a real time basis. This solves the problem of having to spend time to develop a colorimetric response and avoids having to send the blood to a laboratory to determine the value of the desired blood parameter.

Various non-invasive instruments have been developed to measure the blood glucose value using different technology approaches such as optical, electrical Impedance, thermal and electromagnetic technology. For example, LEIN Applied Diagnostics, an United Kingdom based company, has developed a non-invasive optical device that scans the human eye to measure glucose level. To date, none of the none-invasive approaches has been totally successful in providing an instrument for achieving accurate glucose measurement in a manner that is patient friendly in requiring no invasion of the body and that is easy to use, gives results with a degree of accuracy that is satisfactory for use, and that can be built at a relatively low cost. Attempts also have been made to develop instruments for non-invasively measuring the blood hematocrit parameter but none has been entirely successful in the combined aspects of ease-of-use, accuracy and low cost of manufacture.

Accordingly, it would be desirable to provide an apparatus and method that can be used to quickly and accurately determine the sound velocity of a liquid located or flowing in a specimen having at least one deformable wall.

BRIEF DESCRIPTION OF THE INVENTION

The present invention relates to a non-invasive method and apparatus that uses ultrasonic energy to measure the sound velocity of a liquid in a specimen having at least one deformable wall. In accordance with the invention, a sensor makes measurements of the transit time of a signal across the two specimen walls along two acoustic path lengths, whose values do not have to be known, with there being a known differential distance between the first and second path lengths.

The invention can be used in either physical static or dynamic modes of operation. In the physical static mode, a first part of a wall of the specimen is deformed by a known length relative to a second part of the wall and the sensor operates to measure the transit times of the signal along a respective path to each of said first and second parts. In the physical static mode, the measurement of the two transit times can be carried out simultaneously using electronic circuitry to distinguish the signals of the two paths. In the physical dynamic mode, the transit time across the two walls is measured along a first path length. A wall of the specimen is deformed by a known distance to form a second path length across the specimen walls and the transit time of the second path is measured.

The apparatus has electronic circuitry including a microprocessor used to measure is the two transit times. The microprocessor is preprogrammed with the known differential distance. In both the static and dynamic operation modes the sound velocity of the liquid is calculated from the two measured transit times and the known differential distance between the paths. In the invention the signal used to measure the transit time is produced by a transducer that transmits the signal through one wall of the specimen. In both the static and dynamic modes, the transit times can be measured using either using a pulse echo technique in which the signal is reflected from a reflector on the exterior of the specimen wall opposing the wall on which the transducers mounted or by a direct measurement between transducers on the opposing specimen walls. In both the static and dynamic modes it is preferred that the temperature of the liquid be measured and used to correct sound velocity variation due to temperature. Thereafter the temperature corrected measured sound velocity value is used either directly or in association with one or more appropriate and suitable computer algorithms to determine and calculate various physical parameters of the liquid.

In a preferred embodiment of the invention for measuring a blood parameter, the sensor is integrated with a clip that is to be attached to the earlobe which provides a tissue specimen having two walls between which blood is located. The clip easily fits over the earlobe and has a part that engages one of the earlobe walls to deform it thereby providing the paths of two different lengths for the ultrasonic energy to travel. The sensor includes a transducer which transmits pulses of ultrasonic energy through one wall of the earlobe to a reflector from which it is reflected back through the earlobe to the transducer. For static mode operation the reflector has two sections, one of which is flat and the other a projection which deforms one wall of the earlobe by a known differential distance This provides travel paths of two different distances for the signal energy, thereby making two different round-trip transit times of the energy transmitted by the transducer and reflected back to it. In a dynamic mode of this embodiment the reflector is moved by the known differential distance to produce the two different path lengths.

In embodiments of the invention operating in the dynamic mode a position control module is provided that has a part that engages the specimen deformable wall. The part that engages can be either a reflector or a second transducer to receive the energy from the transmitting transducer. Here, the position control module moves the part that it carries by the known differential distance to change the acoustic path length.

All of the embodiments of the invention utilize a controller or a pre-programmed microprocessor. For the embodiments operating in the static mode, the microprocessor is pre-programmed with the known distance differential between the reflector flat and projection sections. For those embodiments operating in the dynamic mode, microprocessor controls the position control module which has a device such as a micro motor or a metal memory element to move the reflector was second transducer the required known differential distance to establish the first and second acoustic path different lengths.

In all of the embodiments the microprocessor controls transmission of the ultrasonic energy signals from the sensor transducer to be transmitted across the walls of the specimen and measures the two different transit times of the two different acoustic path lengths. With the known value of the differential distance of the two acoustic path lengths and the measured values of the two transit times the sound velocity of the liquid in the specimen can be determined.

The apparatus of the invention does not require knowing the thickness of the specimen, be it either tissue or deformable tubing. In all the embodiments of the invention, the liquid can be either static (not moving) or moving.

BRIEF DESCRIPTION OF THE DRAWINGS

Other objects and advantages of the present invention will become more apparent upon reference to the following specification and annexed drawings in which:

FIG. 6 is a top cross-sectional view of another embodiment of the invention;

FIG. 6A is an end view of the tubing of FIG. 6; and

FIG. 7 is a top-cross section of a variation of the embodiment of FIG. 6 including a schematic diagram of the electronic circuit.

DETAILED DESCRIPTION OF THE INVENTION

Figure 1:
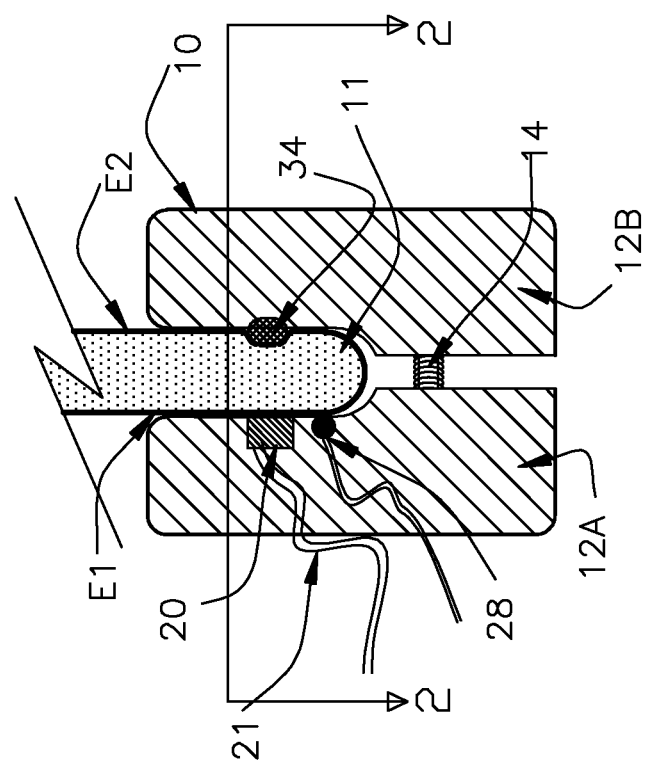
FIG. 1 is a side view of the sensor in cross-section in the form of a clip to be mounted or an earlobe.
Figure 2:
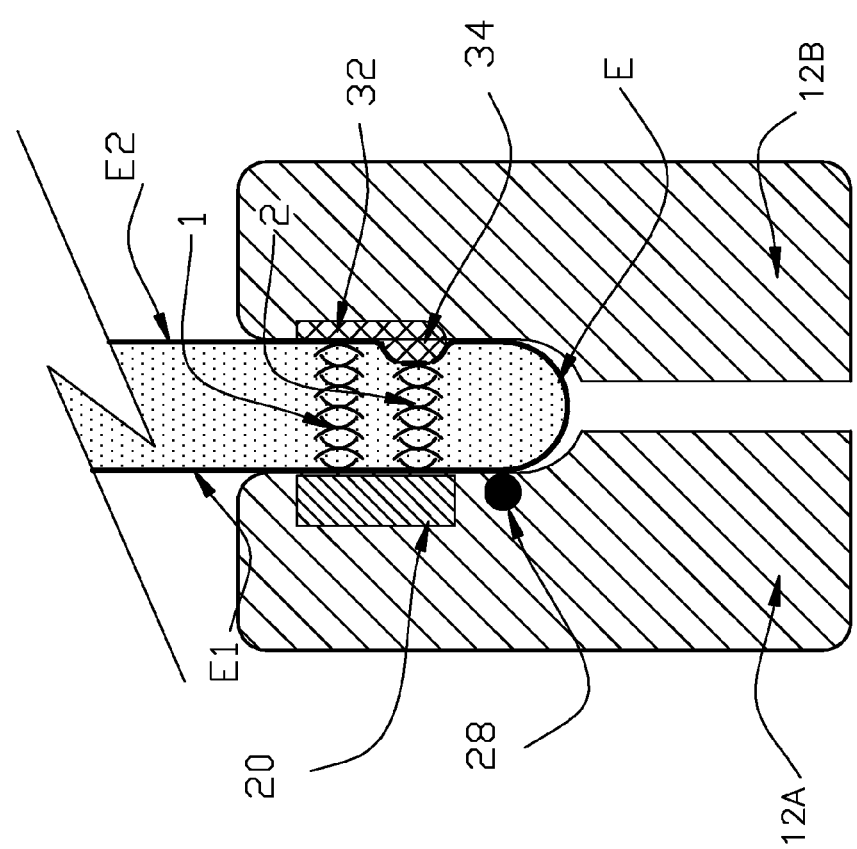
FIG. 2 is a top view of the sensor taken along lines 2-2 of FIG. 1.
Figure 3:
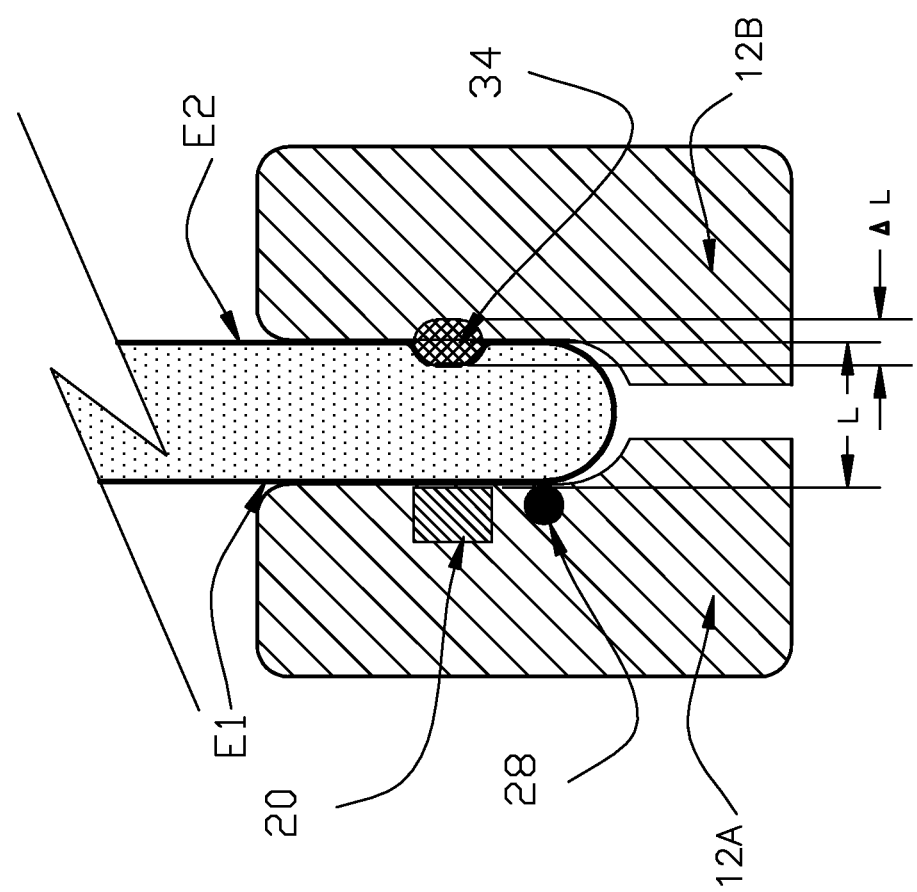
FIG. 3 is a side elevational view of the sensor in cross-section and diagrammatic form showing various details of the distances of interest.

FIGS. 1-3 illustrate an embodiment of the invention operating in the static mode. Here, a sensor 10 for measuring the sound velocity of blood in a tissue specimen is shown. The tissue specimen is illustratively shown as being the earlobe of a human that has opposing interior and anterior walls E1 and E2 forming a chamber between which a volume of blood 11 is collected. It should be understood that the method and apparatus of the invention can be used with other tissue specimens of other parts of the human body, for example, a part of the thigh. The sensor 10 also can be used on the tissue of animals. Further, it could be used on deformable tubing in which the liquid is in either a static or flowing state.

The sensor 10 includes a housing 12 of a suitable material, such as plastic. In a preferred embodiment of the invention illustratively shown, the housing 12 is of two sections 12A and 12B connected together by the spring 14 much in the manner of a conventional spring type clothes pin. The two sections form a slot 16 at the upper part of the housing 12 into which the specimen, here illustratively the earlobe, is inserted. The spring 14 can be of metal and permits the two housing sections to move relative to each other so that the clip can be placed over the specimen. The two section housing and the spring 14 are optional to permit the sensor to be used with specimens of different thicknesses. As an alternative, housings 12 can be of unitary construction and made of different sizes. Also the housing can be custom fitted for a tissue specimen of a particular patient or a certain size tubing.

An ultrasonic transducer 20 is mounted on the wall of the of the housing section 12A facing the slot 16. The ultrasonic transducer 20 can be of any suitable material such as PZT, PET-5A, K-81, DL-31 or PVDF. The transducer 20 is somewhat elongated. The transducer 20 is to lie along a part of one wall, illustratively shown as the interior wall E1 of the earlobe and is to transmit ultrasonic to two points spaced apart on the outside of the opposing anterior earlobe wall E2 and be reflected back to it. The sensor housing can be reversed so that the transducer 20 lies along the anterior wall rather than the interior wall. In a preferred embodiment of the clip type sensor to be used on an earlobe, the sensor is constructed such that the transducer 20 lies across the width of the earlobe wall as shown in the drawings. However, it also can be rotated by 90° from what is shown to lie along the earlobe length. The transducer 20 is mounted in a depression in the wall of the housing section 12A by a suitable adhesive or is molded into the housing section as it is formed. The face of the transducer 20 is to contact one wall of the specimen, as shown.

A temperature sensor 28 also is mounted in the same wall of the housing section 12A as the transducer 20. The temperature sensor 28 is illustratively shown as a wire, which can be a platinum thermocouple wire. Electrical leads 21 extend through the housing to connect the transducer 20 and the temperature sensor 28 to various electronic components, as described below.

An elongated reflector 30 is mounted on the opposite wall of the slot 16 in the housing section 12B. The reflector 30 can be of any suitable material such as plastic or metal. The reflector 30 can be a separate piece mounted in the wall of the housing section 12B or the housing wall candy machine or cast to have the reflector. Reflector 30 has two segments 32 and 34 that are exposed to contact the specimen wall. The first segment 32 is a flat strip and the second is a projection 34 extending from the flat strip 32 into the specimen wall E2. The reflector 30 is located across the width of the specimen wall directly opposing and aligned with the transducer 20. As shown in FIG. 2, when the specimen is an earlobe that is placed in the slot 16 the part of the earlobe wall E2 engaged by the reflector 30 flat strip 32 is deformed inwardly slightly because of the spring pressure of the two housing sections. The part engaged by the projection 34 will be deformed a greater distance inwardly toward the opposing transducer 20 face. The differential distance between the two parts of the earlobe specimen wall engaged by the reflector flat strip 32 and projection 34 is known. This differential distance establishes two different acoustic path lengths for the ultrasonic signals from transducer 20 to travel.

As also is shown in FIG. 2, when the transducer 20 transmits a pulse, or a burst of pulses, of ultrasonic energy signals they will be transmitted through the specimen wall E1 adjacent the transducer 20, through the blood 11, through the other specimen wall E2 and then hit the reflector segments 32 and 34. The ultrasonic energy signal is reflected back to the transducer 20 along the reverse path. The transducer 20 converts the received reflected ultrasonic energy signals into electrical signals that can be processed by suitable electronic circuitry. This is described below.

The embodiment of FIGS. 1-3 operates in the pulse-echo manner and only one active transducer 20 is used. Since the ultrasonic energy signals transmitted by the transducer 20 impinge on both the flat strip reflector segment 32 and the reflector projection segment 34 there will be acoustic travel paths of two different lengths for the ultrasonic energy signal to travel from the transducer 20 and be reflected back to it. The two paths are shown in FIG. 2 as 1, transducer 20 to the reflector 30 flat segment 32, and 2, transducer 20 to the reflector projection segment 34. The round-trip transit time on the ultrasonic energy signal from transducer 20 along path 1 and back to it after reflection from the reflector flat segment 32 will be longer than that of the round-trip travel time of the ultrasonic signal along path 2 because of the reflector projection 34.

The physical difference in length, ΔL, between the face of the reflector flat segment 32 and the tip of the projection 34 from which the ultrasonic energy signal is reflected is shown in FIG. 3 and is known from the construction of the reflector 30. Therefore, a factor related to the ultrasonic energy signal travel time difference along paths 1 and 2 is known. This factor is pre-programmed into a microprocessor to be used in measuring the round-trip transit times of the energy signal along both the paths 1 and 2 as well as calculation of the sound velocity of the blood. This is described below.

Calculation of the round-trip travel time of the ultrasonic energy signal in each of the paths 1 and 2 is described below referring to FIG. 3. For any individual earlobe or other specimen having an overall thickness L:

$$V = \frac{2L}{t_1} = 2\frac{(L-\Delta L)}{t_2} \quad (1)$$

so that $$t_2 L = t_1 L - \Delta L t_1 \quad (2)$$

and $$L(t_1 - t_2) = \Delta L t_1 \quad (3)$$

where:

V=the sound velocity of the liquid. This will be the same for both paths 1 and 2.

L=the thickness of the specimen, which is unknown and he not be known. The signal travels a distance 2L and 2(L−ΔL) because it makes a round-trip.

ΔL=known differential distance between the flat and projection of the reflector.

$t_1$=round trip transit time along path 1 between the transducer 20 and reflector flat segment 32

$t_2$=round trip transit time along path 2 between the transducer 20 and the reflected projection segment 34.

Let:

$$\Delta t = t_1 - t_2$$

so that, from equation (3):

$$L = \frac{\Delta L}{\Delta t} \times t_1 \quad (4)$$

Since L is now known, V is determined from equation (1).

In the operation of the method and apparatus, a microprocessor is used that is preprogrammed with the known value ΔL. The microprocessor also is preprogrammed to operate other circuits to transmit the ultrasonic energy signal and receive it after reflection. It is also preprogrammed to make the round-trip transit time measurements of $t_1$ and $t_2$. Knowing the two round-trip transit times, the microprocessor then computes Δt. With ΔL, Δt and $t_1$ now being known, the value of L is computed by the microprocessor using equation (4) and from this V is calculated from equation (1). All of the instructions need to perform the various measurements and calculations are pre-programmed into the microprocessor, as it is conventional in the art. It should be noted that the computation of the sound velocity V is made without knowing the thickness L of the earlobe tissue specimen. Also, the thickness or composition of the specimen, illustratively the earlobe, walls is not a factor that needs to be known in computing V.

Figure 4:
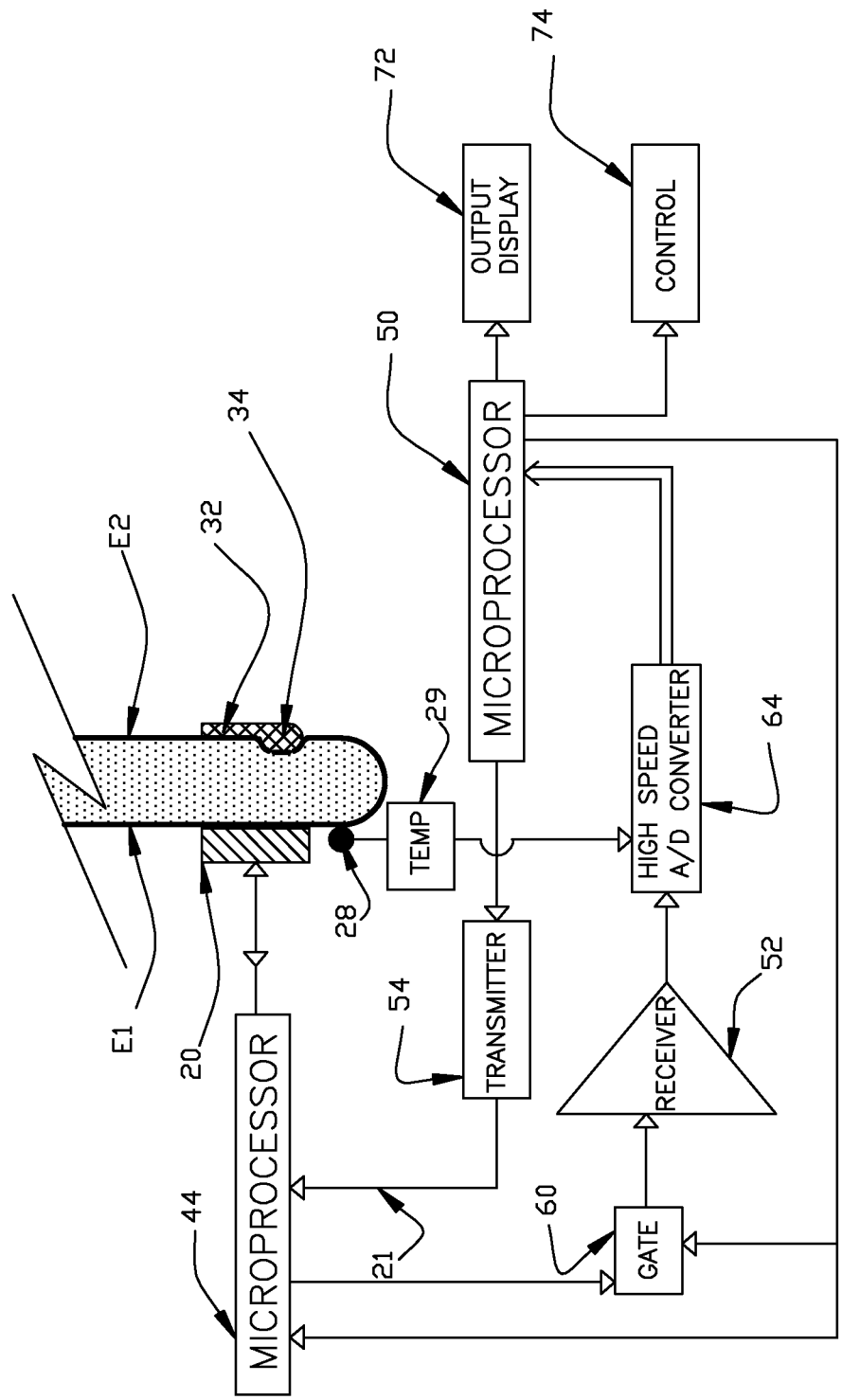
FIG. 4 is a schematic block diagram of the overall apparatus including the electronic circuitry.

FIG. 4 is a schematic block diagram of the electronic circuit used with the sensor 10 of FIGS. 1-3. The circuit includes a conventional programmable microprocessor 50 or controller that preferably has its own digital signal processor and internal RAM/ROM memory. Of course, circuitry with separate memory and processor elements can be used. The microprocessor controls a multiplexer 44 which directs the various signals during the operation of the circuit in both the transmit and receive modes. The microprocessor 50 controls a transmit energy source 54 to produce single pulses or bursts of pulses of electrical signals in the ultrasonic frequency range at predetermined time spaced intervals. The electrical signals are applied to the transducer 20 through multiplexer 44 which operates the circuit in transmit mode. The transducer 20 converts the electrical signals into ultrasonic energy (electro-mechanical) signals. The ultrasonic energy signals are transmitted through the interior specimen wall E1, the liquid 11 in the specimen, through the anterior wall E2 to the reflector segments 32 and 34, which return the signals back to the transducer 20 along the reverse path. The transducer 20 converts the ultrasonic energy signals reflected back to it by the reflector 30 segments along the two different paths 1 and 2 into electrical signals. These are applied to the multiplexer 44 which is now operating the circuit in receive mode. The electrical signals are directed by the multiplexer to a gating circuit 60 that is operated by the microprocessor 50 to selectively pass the signals of the signal paths 1 and 2 returned from the reflector 30.

In a preferred embodiment of the invention, the reflector projection 34, preferably further depresses the specimen wall E2 by about 15%-45% as compared to the depression of the wall by the reflector flat strip segment 32. The amount of depression depends upon the type of materials of the specimen walls and the type of liquid between them. The travel times of the signals in the paths 1 and 2 will differ by about the amount of the depression difference. This provides sufficient time for the differentiation of the signals of the two paths for selection by the gating circuit 60 so that there will be separate processing in measuring the different round-trip transit times $t_1$ and $t_2$ of paths 1 and 2. If desired the gating circuit 60 can be part of the multiplexer 44. The signals from the gating circuit 60 output are applied to a receiver circuit 52 which preferably has a high gain amplifier and then to a high speed analog/digital converter 64.

Since the microprocessor controls the time of transmission of the ultrasonic energy signals from the transducer 20 and measures the time of reception of the signals from the paths 1 and 2 it can calculate each of the round-trip travel times $t_1$ and $t_2$. During a first gating window the signals returned from the shorter distance travel path 2 from the reflector projection segment 34 will be passed from the receiver amplifier 52 to the high speed analog to digital converter 64. The digital signal output is applied to the microprocessor 50 for use in measuring the path 2 round-trip transit time $t_2$. Similarly, during a second and later gating window, the signal from the longer distance travel path 1 will be passed to the analog to digital converter 64 and then to the microprocessor 50 to measure the path 1 round-trip transit time $t_1$. Depending upon the operating frequency of the ultrasonic energy signal and other factors, the two signals from the pats 1 and 2 can be differentiated successfully in the analog/digital converter 64.

The microprocessor is preprogrammed with the known numerical value ΔL as discussed above. From the measured values of $t_1$ and $t_2$ and the known value of ΔL the microprocessor computes V. In a preferred embodiment of the invention the value of V is temperature corrected before being used in further applications to improve accuracy of application results obtained based upon the computed sound velocity V. To do this the temperature sensor 20 is connected to a suitable electronic circuit 29 that produces an analog signal value of the measured temperature. The analog signal is applied to the analog/digital converter 64 to produce a digital temperature value that is applied to the microprocessor 50. By using an approximate analytical model of salt water, see, J. Lubber and R. Grabber Ultrasonic Medical Biology, vol 24 page 1065 (1998), that is pre-programmed into the microprocessor 50 a temperature corrected value of V is produced that can be used in other applications such as to analyze various parameters of the liquid. Several of these are explained below.

The microprocessor 50 of the electronic circuit has an output 72 which can be digital or analog signals provided to other apparatus that utilize the calculations produced by the microprocessor. The output also can be a visual display of any conventional type which can display a numerical value for the calculated sound velocity or any other property of the liquid computed by the microprocessor utilizing preprogrammed algorithms corresponding to the property. The display would be in the appropriate units corresponding to the sound velocity and/or liquid property.

A typical application of the invention in which the liquid whose sound velocity is determined is blood. Here, the microprocessor 50 is preprogrammed with one or more algorithms depending upon the blood parameter that is to be measured or monitored. Two such parameters, glucose and hematocrit, are discussed below as examples. Other parameters also can be monitored based upon a relationship of the particular parameter to the blood sound velocity.

U.S. Patent Publication US 2007/0255141 teaches that changes in glucose can be evaluated indirectly by measurement of the sound velocity through the tissue but does not measure the sound velocity of the blood itself.

Information relating sound velocity of blood and glucose concentration is available such as found in Tables 23, 26 and 29 of the publication "Partial Molar Properties of Aqueous Monoshccharide Solutions at Elevated Pressure", Asbjorn Aarfloat, Cand. Scient. Thesis Physical Chemistry; Dept. Of Chemistry; University of Bergen, Norway; March 2001. This publication describes the relationship of molality of glucose concentration (mol/kg—moles of solute divided by the kilograms of solvent) and sound velocity (meter/sec). From the data in these tables a linear relationship is shown to exist between the sound velocity V and the glucose concentration, hereafter designated "g", from which the following algorithm used by the microprocessor is constructed.

$$V = 1496.5 + 0.0036\,g - 7 \times 10^{-8}\,g^2 \qquad (5)$$

In the equation

V=the sound velocity in meter/sec and g=the glucose concentration in mg/dl (milligrams/deciliter)

Since V is known as calculated by the microprocessor in accordance with equations (1)-(4), the glucose concentration g is calculated by the microprocessor and displayed. Upon equation (5) being solved, the results can be converted by the microprocessor to be in the units desired for display or any other purpose.

The sound velocity V of blood serum is affected by change in temperature. Therefore, it is first temperature corrected in the manner described above before being used to calculate the blood glucose concentration g using equation (5).

Considering another blood parameter, the blood hematocrit level is calculated by the microprocessor using an empirical relationship between the measured sound velocity and the blood hematocrit value such as:

$$Vc = 1499.46 + 0.887\,HCT \qquad (6)$$

Where,

HCT=hematocrit level in percentage

Vc=blood sound velocity as determined by equations (1)-(4) corrected according to a temperature reference model that is pre-programmed in the microprocessor as explained above. Equation (6) and the temperature model are programmed into the microprocessor for execution with the temperature being measured by the temperature sensor 28 of the sensor 10.

An appropriate equation to calculate TPC (total protein concentration) also can be programmed into the microprocessor. One such equation is:

$$V = 1482.26 + 1.54\,T + 0.51\,HCT + 2.8\,TPC \qquad (7)$$

Where

V: blood sound velocity as per equations (1)-(4)

T: temperature measured in centigrade as measured by sensor 28

HCT: hematocrit as per equation (6)

Sacerio, "Determination of Velocity Ultrasonics in Whole Human Blood", 25th Annu. Conf. Eng, Med. Biol., Alliance for Engineering in Medicine and Biology, Bethesda, Md., October 1972, page 39; Bradley, D. L. and Sacerio, J. L. "The Velocity of Ultrasound in Human Blood under Varying the Physiologic Parameters", J. Surg. Res., 12, 290, 1972).

Knowing the hematocrit and total protein contents, the blood hemoglobin can be calculated.

Typical operating parameters for the apparatus are:

| | |
|---|---|
| thickness of earlobe | 3.5-6.0 mm. |
| ΔL | 0.5-2.5 mm | frequency of bursts of transmitted ultrasonic energy signal 3 MHz to 50 MHZ

| | |
|---|---|
| duration of signal bursts | 50 nano seconds to 1 μs |
| time between bursts | 50 μs to 5 ms |

Figure 5:
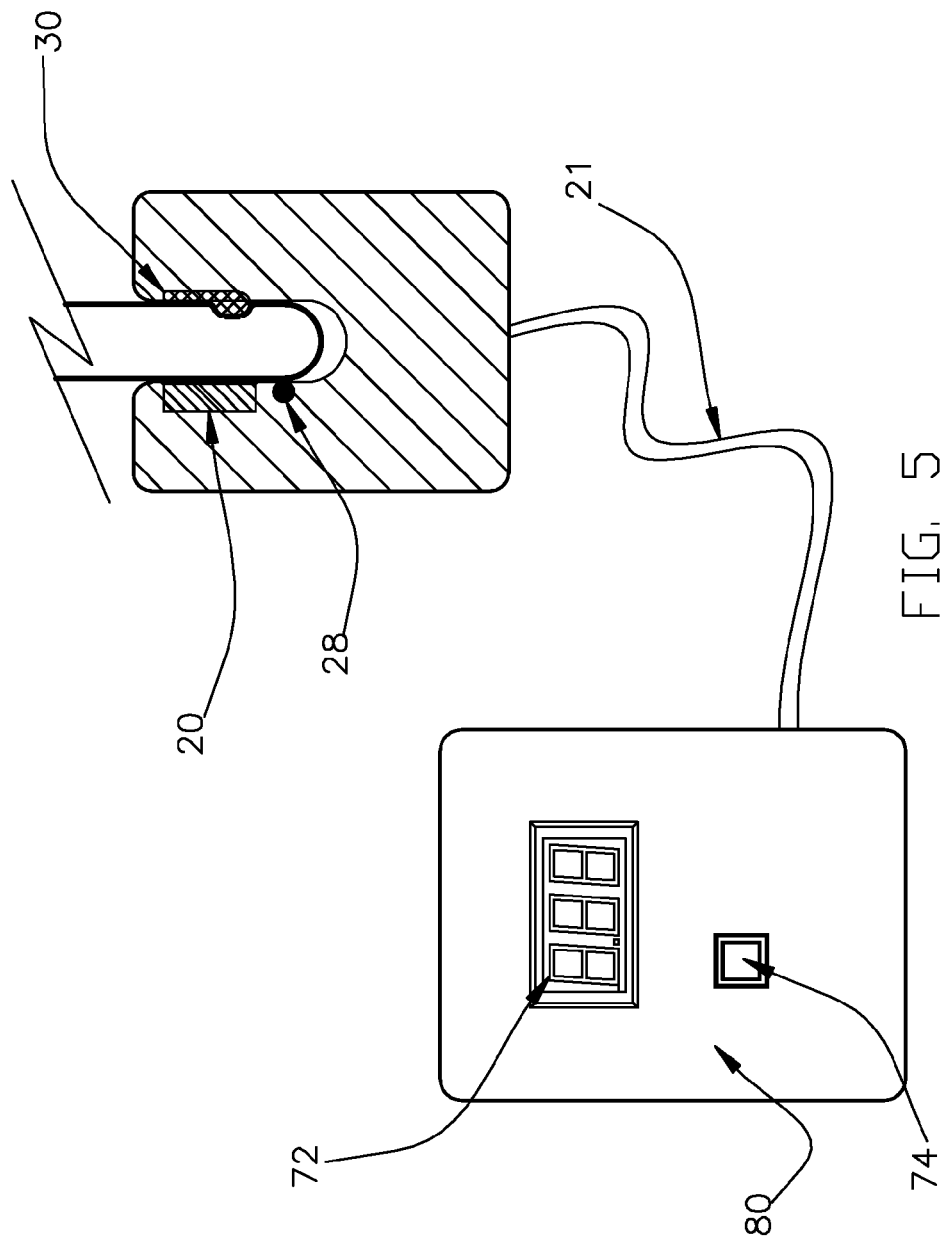
FIG. 5 Is a view of the apparatus including a case for housing the various electronic components.

All of the components of the electronic circuit of FIG. 4 can be contained in a case 80, as shown in FIG. 5, to which the transducer 20 and temperature sensor 28 are connected by the lead wires 21 of the sensor 10. The apparatus case 80 also includes a display 72 and a control 74 that are mounted on the case. The display 72 will display the value of the sound velocity or of the corresponding liquid parameter that is computed by the microprocessor 50 calculated from the sound velocity according to one or more preprogrammed algorithms. The control 74 is used to turn the apparatus on and off. If the apparatus is built with the functionality of computing two or more liquid parameters, such as glucose and hematocrit values when the liquid is blood, then the control 74 will be used to selectively switch the microprocessor to compute the desired parameter whose value will then be displayed on the display 72.

A dynamic type apparatus embodiment of the invention is illustrated in FIG. 6. In this embodiment the specimen is illustrated as being a tube 90 of deformable material, such as any of the numerous types of plastics that are used in medical and industrial applications. The specimen also can be a tissue specimen such as an earlobe as described above. Here, the sensor housing has walls 81A and 81B that define the slot 16 within which the specimen 90 is placed. As illustrated with respect to FIG. 1, the housing walls 81 can be part of articulated sections such as the clip designed for the earlobe shown in FIGS. 1-3. Here, the housing sections would be clamped over the deformable tubing specimen 90.

As in the previous embodiments, the transducer 20 is mounted in the housing wall 81A and there are leads 21 connecting it to the electronic circuitry. The electronics are basically those as described with respect to FIG. 4. There also can be a temperature sensor wire, such as 28, although not shown here. A precision position control module 82 is mounted in the housing wall 81B opposing the transducer 20. The position control module 82 is a device that can move linearly by a precise predetermined amount and is connected by leads 22 to the electronic circuit microprocessor. Suitable devices for the position control module 82 include micro motors, memory type metals, etc. The module 82 preferably also produces a position feedback signal to indicate how far that it moves so that the microprocessor can make suitable adjustments in control to ensure the correct amount of movement. As in the previous embodiments, all of the electronic components can be located in a suitable case or housing, such as shown in FIG. 5, for control of the apparatus by an operator or user.

The position control module 82 has an output shaft 84 that carries a reflector 86 that is a flat piece of metal or plastic. The reflector 86 opposes the ultrasonic transducer 20 across the sensing head gap 16 and the two specimen walls. The position controller 82 is mounted in the head 81 so that the shaft 84 and the reflector 86 that it carries are free to move transverse to the gap 16 width and move the reflector 86 into and out of the gap 16 against a wall of the specimen be it tissue such as an earlobe or the deformable tubing 90 that is illustrated. The initial position of the reflector 86 outer face that engages the specimen preferably is flush along the length of the wall 81B.

In this embodiment the specimen such as the tubing 90 is inserted into the measuring head gap 16 and the position control module 82 set so that the reflector 86 outer face is flush along the length of the wall 81B and engages a wall of the specimen in an undeformed condition or state. At this time, as shown in FIG. 6A, the distance from the transducer 20 to the reflector 86 has a distance or length L, the diameter of the tubing 90. This corresponds to the first path length 1 for signals transmitted from the transducer 20 to the reflector 86 for reflection back to the transducer 20. The microprocessor 50 is programmed so that at this time an ultrasonic energy signal is transmitted across the specimen walls and a first measurement is made that is the round trip transit time $t_1$.

After $t_1$ is measured the microprocessor operates the position control module 82 to move the reflector 86 further into the gap 16 by a known distance. This deforms or moves the specimen wall engaged by the reflector 86 by the known fixed distance closer to the ultrasonic transducer 20. The known distance of movement of the reflector 86 and the specimen wall that it engages is $\Delta L$, as shown in FIG. 6A. This known distance is programmed into the microprocessor. The distance of movement of the reflector 86 by the position control module 82 corresponds to the distance $\Delta L$ resulting from the construction of the flat and projecting parts of the two segment reflector 30 in the embodiments of FIGS. 1-3.

Movement of the reflector 86 is stopped by the microprocessor controlled position control module with the reflector 86 in the desired more inward position. At this time the specimen has a transverse length that corresponds to the path length 2. The microprocessor 50 initiates a second measurement of the round-trip transit time and measures the second transit time $t_2$. Having been pre-programmed with $\Delta L$, the differential distance of the two signal path lengths, and having measured $t_1$ and $t_2$ the microprocessor 50 calculates the sound velocity V in accordance with equations (1)-(4) described above. In this embodiment the electronic circuit is basically the same as that shown in FIG. 4 with the gating circuit 60 being replaced by the sequential operation to measure $t_1$ and $t_2$ at the two different positions of the reflector 86. As previously described, the microprocessor can be programmed with a temperature correction program for the liquid and various algorithms to calculate various parameter of the liquid be it blood or another liquid. Also, the electronics can be in a case having a display to display the appropriate quantities of the parameter and a control to select the algorithm.

FIG. 7 shows an alternate of the embodiment of FIG. 6 with the same reference numerals for the same components of all of the other embodiments of the invention used as applicable. Here, the reflector opposite the transducer 20 is replaced by a transducer 98 to receive the ultrasonic energy transmitted by transducer 20. The position control module 82 as directed by the microprocessor 50 moves the transducer 98 from a first position flush with the housing wall 81B and engaging the undeformed specimen 90 wall to a second position with the movement distance being such as to change the specimen transverse length L by a predetermined known distance amount $\Delta L$. As in the embodiment of FIG. 6 the first position of the movable transducer 96 establishes the first acoustic path length 1 between the two transducers 20 and 96 and the second position establishes the second acoustic path length 2.

With the transducer 96 being in the first position and the specimen 90 having the transverse length L (path length 1), a measurement of the transit time $t_1$ of the ultrasonic energy from the transducer 20 through the two walls of the specimen 90 to the transducer 96 is made by the microprocessor. Similarly, upon the position control module 82 having moved the transducer 96 to the second position wherein the transverse length of the specimen 90 has been changed by the known desired distance $\Delta L$ (path length 2) a measurement of the transit time $t_2$ is made.

The embodiment of FIG. 7 differs from that of FIGS. 1-4 and 6 in that only a one-way, and not a round-trip, measurement of the transit time across the walls of the specimen is made. Also, it is a direct transmission technique and not pulse echo. The mathematics of equations (1)-(4) discussed above apply here in the same way in calculating the sound velocity V with suitable modifications to go from measuring a round-trip transit time to a one-way trip transit time. This is shown below:

$$V = \frac{L}{t_1} = \frac{(L - \Delta L)}{t_2} \tag{1a}$$

so that $$t_2 L = t_1 L - \Delta L t_1 \tag{2a}$$

and $$L(t_1 - t_2) = \Delta L t_1 \tag{3a}$$

where:
V=the sound velocity. This will be the same for both paths 1 and 2.
L=the thickness, or transverse length, of the specimen, which is unknown. The signal from transducer 20 to transducer 96 travels a distance L.
ΔL=change in the specimen transverse length, which is the known distance of movement of the transducer 96 between the first and second positions.
$t_1$=transit time along path 1 between the transducer 20 and transducer 96.
$t_2$=transit time along path 2 between the transducer 20 and the transducer 96.

$$\Delta t = t_1 - t_2$$

Thus, from equation (3a):

$$L = \frac{\Delta L}{\Delta t} \times t_1 \quad (4a)$$

As before, the microprocessor 50 knows the value ΔL and has measured $t_1$ and $t_2$. Therefore, it can calculate the sound velocity V and having been supplied with the necessary temperature correction program and algorithms can calculate a selected characteristic or parameter of the liquid.

The embodiments of FIGS. 6 and 7 have an advantage in that they are dynamic. That is, the flow of liquid through the specimen is constricted for only the time that the reflector 86 or transducer 96 has been moved inwardly of the measuring head gap 16 to the second position.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. Apparatus for determining the sound velocity of blood in a specimen as a measure of the glucose value of the blood, said specimen having two walls between which the blood is contained and with one of the specimen walls being deformable, comprising:
a housing having a slot therein formed by first and second walls into which the specimen is placed, said housing being without any portion extending through the specimen;
a sensor including a transducer for transmitting ultrasonic energy signals between the two walls of the specimen;
deforming apparatus of said housing for deforming said one wall of the specimen by a known distance from a first position spaced from said transducer to a second position closer to said transducer; and
an electronic circuit including a microprocessor for measuring a respective first and second transit time of said ultrasonic energy signals through the blood between the two walls of the specimen for each of said first and second positions of the deformable specimen wall, and for calculating the sound velocity of the blood based upon said known distance and the said measured first and second transit times, and determining the glucose value of the blood.

2. The apparatus as claimed in claim 1 wherein said microprocessor calculates the sound velocity in accordance with the formula $$V = \frac{L}{t_1} = \frac{(L - \Delta L)}{t_2}$$

where
L=the thickness of the specimen, which is originally unknown
ΔL=known distance between said first and second positions of the deformable wall
$t_1$=transit time of the signals from said transducer though the liquid with said deformable wall being in the first position
$t_2$=transit time of the signals from the transducer though the liquid with said deformable wall being in the second position, and where $$L(t_1 - t_2) = \Delta L t_1, \text{ or}$$
$$L = \frac{\Delta L}{\Delta t} \times t_1.$$

3. The apparatus as claimed in claim 1 wherein said deforming apparatus comprises:
a reflector located in a wall of the housing and engaging the exterior of the specimen deformable wall, said reflector having a first segment with a flat strip and a second segment with a projection extending from said flat strip by said known distance, said projection comprising at least part of said deforming apparatus and wherein said ultrasonic energy signal is transmitted through both specimen walls and reflected from both said reflector segments back to said transducer through the liquid and the two walls of the specimen.

4. The apparatus as claimed in claim 3 wherein said electronic circuit further comprises:
a gating circuit for selecting the signal reflected back to said transducer for use in calculating each of said first and second transit times.

5. The apparatus as claimed in claim 1 wherein said deforming apparatus comprises:
a position control module located in a wall of the housing and having a part that engages the exterior of the specimen deformable wall and is operable to move the part to deform the wall from said first position by said known distance to said second position.

6. The apparatus as claimed in claim 5 wherein said part comprises:
a reflector that reflects said signal back to said transducer and wherein said electronic circuit operates to measure said first and second transit times sequentially with the specimen deformable wall at said corresponding first and second positions.

7. The apparatus as claimed in claim 5 wherein said part comprises:
a second transducer that receives the signal from said transducer transmitting said ultrasonic energy signals upon the specimen deformable wall being at each of said first and second positions, and said electronic circuit operates to measure said first and second transit times sequentially with the specimen deformable wall being at said first and second positions.

8. The apparatus as claimed in claim 1 wherein the specimen is a flexible tube carrying a patient's blood.

9. The apparatus as claimed in claim 1
wherein said transducer transmitting said ultrasonic energy signals is mounted in one of said walls of said slot to interact with one wall of the specimen;
wherein said deforming apparatus includes a reflector mounted in the other of said slot walls to reflect said signal back to said transducer, said reflector having a first segment with a flat strip and a second segment with a projection extending from said flat strip by said known distance, said ultrasonic energy signal being transmitted through both specimen walls and reflected from both said reflector segments back to said transducer through the two specimen walls;
wherein said specimen is a portion of a patient's body that fits in the slot, the blood that is measured is the blood of the patient in that portion of the patient's body, and the measurement is made in real time without contacting the blood.

10. Apparatus for non-invasive determination of the sound velocity of blood in a specimen as a measure of at least one of the glucose and hematocrit value of the blood, said specimen having two walls between which the blood is contained and with one of the specimen walls being deformable, comprising:
a housing having a slot therein formed by first and second walls into which the specimen is placed, said housing being without any portion extending through the specimen;
a sensor including a transducer transmitting said ultrasonic energy signals being mounted in one of said walls of said slot to interact with one wall of the specimen;
deforming apparatus for deforming said one wall of the specimen by a known distance from a first position spaced from said transducer to a second position closer to said transducer, said deforming apparatus including a reflector mounted in the other of said slot walls to reflect said signal back to said transducer, said reflector having a first segment with a flat strip and a second segment with a projection extending from said flat strip by said known distance, said ultrasonic energy signal being transmitted through both specimen walls and reflected from both said reflector segments back to said transducer through the two specimen walls and
an electronic circuit including a microprocessor measuring a respective first and second transit time of said ultrasonic energy signals through the blood between the two specimen walls for each of said first and second positions of the deformable specimen wall, calculating the sound velocity of the blood based upon said known distance and the said measured first and second transit times, and determining at least one of the glucose and hematocrit values of the blood;
wherein said specimen is a portion of a patient's body that fits in the slot, the blood that is measured is the blood of the patient in that portion of the patient's body, and the measurement is made without contacting the blood.

11. The apparatus as claimed in claim 10 further comprising:
a reflector mounted in the other of said slot walls to reflect said signal back to said transducer.

12. The apparatus as claimed in claim 11 wherein said reflector comprises:
a first segment with a flat strip and a second segment with a projection extending from said flat strip by said known distance, and
wherein said ultrasonic energy signal is transmitted through both specimen walls and reflected from both said reflector segments back to said transducer through the two specimen walls.

13. The apparatus as claimed in claim 12 wherein said electronic circuit further comprises:
a gating circuit for selecting the signal reflected back to said transducer for use in calculating each of said first and second transit times.

14. The apparatus as claimed in claim 10 wherein said deforming apparatus comprises:
a position control module having a part that engages the exterior of the specimen deformable wall and is operable to move the part to deform the wall from said first position by said known distance to said second position.

15. The apparatus as claimed in claim 14 wherein said part comprises:
a reflector that reflects said signal back to said transducer and wherein said electronic circuit operates to measure said first and second transit times sequentially with the specimen deformable wall at said corresponding first and second positions.

16. The apparatus as claimed in claim 14 wherein said part comprises:
a second transducer that receives the signal from said transducer transmitting said ultrasonic energy signals upon the specimen deformable wall being at each of said first and second positions, and said electronic circuit operates to measure said first and second transit times sequentially with the specimen deformable wall being at said first and second positions.

17. The apparatus as claimed in claim 10 wherein said housing comprises:
first and second sections with each of said housing sections defining a respective wall of said slot, and
a resilient means for connecting said first and second housing sections for permitting said first and second housing sections to a move relative to each other, said sections and resilient means forming an earlobe clip, said specimen being the ear lobe of a patient, and the blood measured being the blood in the patient's earlobe.

18. The apparatus as claimed in claim 17 wherein said deforming apparatus comprises:
a reflector engaging the exterior of the specimen one deformable wall, said reflector having a first segment with a flat strip and a second segment with a projection extending from said flat strip by said known distance, and wherein said ultrasonic energy signal is transmitted through both specimen walls and reflected from both said reflector segments back to said transducer through the liquid and the two walls of the specimen.

19. The apparatus as claimed in claim 17 wherein said deforming apparatus comprises:
a position control module having a part that engages the exterior of the specimen deformable wall and is operable to move the part to deform the wall from said first position by said known distance to said second position.

20. The apparatus as claimed in claim 19 wherein said part comprises:
a reflector that reflects said signal back to said transducer and wherein said electronic circuit operates to measure said first and second transit times sequentially with the specimen deformable wall at said corresponding first and second positions.

21. The apparatus as claimed in claim 19 wherein said part comprises:

a second transducer that receives the signal from said transducer transmitting said ultrasonic energy signals upon the specimen deformable wall being at each of said first and second positions, and said electronic circuit operates to measure said first and second transit times sequentially with the specimen deformable wall being at said first and second positions.

22. Apparatus for determining the sound velocity of blood in a specimen as a measure of the glucose value of the blood, said specimen having two walls between which the blood is contained and with one of the specimen walls being deformable, comprising:
 a sensor including a transducer for transmitting ultrasonic energy signals between the two walls of the specimen;
 deforming apparatus for deforming said one wall of the specimen by a known distance from a first position spaced from said transducer to a second position closer to said transducer; and
 an electronic circuit including a microprocessor for measuring a respective first and second transit time of said ultrasonic energy signals through the blood between the two walls of the specimen for each of said first and second positions of the deformable specimen wall, and for calculating the sound velocity of the blood based upon said known distance and the said measured first and second transit times, and determining the glucose value of the blood; and
 wherein said microprocessor determines the glucose value of the blood in accordance with an algorithm:

$$V=1496.5+0.0036\,g-7\times10^{-8}\,g^2$$

in the equation
 V=blood sound velocity in m/sec (meter/sec) and
 g=the glucose concentration in mg/dl (milligrams/deciliter).

23. Apparatus for non-invasive determination of the sound velocity of blood in a specimen as a measure of at least one of the glucose and hematocrit value of the blood, said specimen having two walls between which the blood is contained and with one of the specimen walls being deformable, comprising:
 a housing having a slot therein formed by first and second walls into which the specimen is placed,
 a sensor including a transducer transmitting said ultrasonic energy signals, said sensor being mounted in one of said walls of said slot to interact with one wall of the specimen;
 deforming apparatus for deforming said one wall of the specimen by a known distance from a first position spaced from said transducer to a second position closer to said transducer, said deforming apparatus including a reflector mounted in the other of said slot walls to reflect said signal back to said transducer, said reflector having a first segment with a flat strip and a second segment with a projection extending from said flat strip by said known distance, said ultrasonic energy signal being transmitted through both specimen walls and reflected from both said reflector segments back to said transducer through the two specimen walls; and
 an electronic circuit including a microprocessor measuring a respective first and second transit time of said ultrasonic energy signals through the blood between the two walls of the specimen for each of said first and second positions of the deformable specimen wall, calculating the sound velocity of the blood based upon said known distance and the said measured first and second transit times, and determining at least one of the glucose and hematocrit values of the blood; and
 wherein said housing comprises first and second sections with each of said housing sections defining a respective wall of said slot, and a resilient means for connecting said first and second housing sections for permitting said first and second housing sections to move relative to each other, said sections and said resilient means forming an earlobe clip, said specimen being the ear lobe of a patient, the blood measured being the blood in the patient's earlobe and the measurement being made without contacting the blood;
 wherein said deforming apparatus comprises a position control module having a part that engages the exterior of the specimen deformable wall and is operable to move the part to deform the wall from said first position by said known distance to said second position;
 wherein said part comprises a reflector that reflects said signal back to said transducer and wherein said electronic circuit operates to measure said first and second transit times sequentially with the specimen deformable wall at said corresponding first and second positions; and
 wherein said microprocessor determines the hematocrit value of the blood in accordance with an algorithm:

$$V=1499.46+0.887\mathrm{HCT} \qquad (6)$$

where,
 HCT=hematocrit level in percentage
 V=blood sound velocity in m/sec.

24. Apparatus for non-invasive determination of the sound velocity of blood in a specimen as a measure of at least one of the glucose and hematocrit value of the blood, said specimen having two walls between which the blood is contained and with one of the specimen walls being deformable, comprising:
 a housing having a slot therein formed by first and second walls into which the specimen is placed;
 a sensor including a transducer transmitting said ultrasonic energy signals being mounted in one of said walls of said slot to interact with one wall of the specimen;
 deforming apparatus for deforming said one wall of the specimen by a known distance from a first position spaced from said transducer to a second position closer to said transducer, said deforming apparatus including a reflector mounted in the other of said slot walls to reflect said signal back to said transducer, said reflector having a first segment with a flat strip and a second segment with a projection extending from said flat strip by said known distance, said ultrasonic energy signal being transmitted through both specimen walls and reflected from both said reflector segments back to said transducer through the two specimen walls; and
 an electronic circuit including a microprocessor measuring a respective first and second transit time of said ultrasonic energy signals through the blood between the two walls of the specimen for each of said first and second positions of the deformable specimen wall, calculating the sound velocity of the blood based upon said known distance and said measured first and second transit times, and determining at least one of the glucose and hematocrit values of the blood;
 wherein said specimen is a portion of a patient's body that fits in the slot, the blood that is measured is the blood of the patient in that portion of the patient's body, and the measurement is made without contacting the blood;

wherein said microprocessor determines the glucose value of the blood in accordance with an algorithm:

$$V = 1496.5 + 0.0036\, g - 7 \times 10^{-8}\, g^2$$

in the equation
V=blood sound velocity in m/sec (meter/sec) and
g=the glucose concentration in mg/dl (milligrams/deciliter).

* * * * *